US005744655A

United States Patent [19]
Thomas et al.

[11] Patent Number: 5,744,655
[45] Date of Patent: Apr. 28, 1998

[54] PROCESS TO MAKE 2,3-DIHALOPROPANOLS

[75] Inventors: P. J. Thomas; R. Garth Pews; Paul C. Vosejpka; George J. Frycek, all of Midland, Mich.

[73] Assignee: The Dow Chemical Company, Midland, Mich.

[21] Appl. No.: 667,526

[22] Filed: Jun. 19, 1996

[51] Int. Cl.$^6$ .................................................. C07C 31/34
[52] U.S. Cl. ........................................................ 568/841
[58] Field of Search .................................. 568/840, 841, 568/842; 502/326

[56] References Cited

U.S. PATENT DOCUMENTS

| | | |
|---|---|---|
| 2,860,146 | 11/1958 | Furman et al. . |
| 3,277,187 | 10/1966 | Dewhirst ............................ 260/633 |
| 3,454,644 | 7/1969 | Dewhirst . |
| 3,935,284 | 1/1976 | Kruse . |
| 4,008,281 | 2/1977 | Knowles et al. . |
| 4,024,193 | 5/1977 | Kruse . |
| 4,049,577 | 9/1977 | Childress et al. . |
| 4,072,720 | 2/1978 | Haag et al. . |
| 4,129,600 | 12/1978 | Childress et al. . |
| 4,166,808 | 9/1979 | Daumas et al. . |
| 5,225,389 | 7/1993 | Caillod et al. . |
| 5,326,916 | 7/1994 | Kobayashi . |

FOREIGN PATENT DOCUMENTS

| | | |
|---|---|---|
| 630238 | 4/1991 | Australia . |
| 1050834 | 2/1989 | Japan . |
| 1052732 | 2/1989 | Japan . |
| 64-50834 | 2/1989 | Japan . |
| 64-52732 | 2/1989 | Japan . |

OTHER PUBLICATIONS

Sanchez–Delgado et al., "Homogeneous Hydrogenation of Aldehydes to Alcohols with Ruthenium Catalysts", Journal of Organometallic Chemistry, vol. 209, No. 1, pp. 77–83 (Apr. 7, 1981).

*Primary Examiner*—Gary Geist
*Assistant Examiner*—Karl J. Puttlitz, Jr.

[57] ABSTRACT

A 2,3-dihalopropanol is made by reacting 2,3-dihalopropanal with a hydrogenating agent in the presence of a transition metal-containing catalyst, under conditions such that 2,3-dihalopropanol is formed. The reaction is particularly useful as Step (3) in a process to make epihalohydrin by:

(1) reacting a 3-carbon hydrocarbon with an oxidizing agent to form acrolein;

(2) reacting acrolein with a molecular halogen to form 2,3-dihalopropanal;

(3) reducing 2,3-dihalopropanal to form 2,3-dihalopropanol; and (4) cyclizing 2,3-dihalopropanol to make epihalohydrin.

The process produces epihalohydrin using only about one mole of halogen per mole of epihalohydrin. It also uses substantially less water than existing processes.

19 Claims, No Drawings

PROCESS TO MAKE 2,3-DIHALOPROPANOLS

BACKGROUND OF THE INVENTION

The present invention relates to the art of making 2,3-dihalopropanols.

2,3-dihalopropanols are usually represented by:

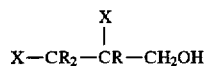

Formula I $$X-CR_2-CR(X)-CH_2OH$$

wherein:

each "X" is independently a halogen atom; and
each "R" is independently a hydrogen atom or an organic group. 2,3-dichloropropanol is the most commonly used member of the class.

2,3-dihalopropanols are important intermediates in the manufacture of epihalohydrin. For instance, epichlorohydrin is usually made by a three-step process of:

(1) reacting propylene and chlorine to make allyl chloride;
(2) reacting allyl chloride with hypochlorous acid to make a mixture of dichloropropanols; and
(3) reacting the dichloropropanols with a strong base to make epichlorohydrin.

This process makes large quantities of halogen-containing waste. For each mole of epichlorohydrin which is produced, at least about two moles of molecular chlorine are required. Each molecule of epichlorohydrin contains one atom of chlorine, and the remaining three atoms of chlorine are lost in the waste stream.

It has been proposed to make epihalohydrins by processes which are more efficient in their use of halogen. For instance, Furman et al. (U.S. Pat. No. 2,860,146 (Nov. 11, 1958)) proposed to make epihalohydrin by a three-step process of:

(1) reacting acrolein with chlorine to form 2,3-dichloropropanal; and
(2) reacting 2,3-dichloropropanal with a secondary alcohol in the presence of a catalyst to form 2,3-dichloropropanol; and
(3) dehydrochlorinating 2,3-dichloropropanol to make epichlorohydrin.

However, the costs associated with this process are too high for it to be economically feasible, due to the cost of recycling alcohol and regenerating catalyst.

What is needed is an economical process to make dihalopropanols with reduced production of halogenated waste.

SUMMARY OF THE INVENTION

One aspect of the present invention is a process to make 2,3-dihalopropanol comprising the step of reacting 2,3-dihalopropanal with a hydrogenating agent in the presence of a transition metal-containing catalyst, under conditions such that 2,3-dihalopropanol is formed.

A second aspect of the present invention is a process to make epihalohydrin comprising the steps of:

(1) reacting a hydrocarbon which contains 3 carbon atoms with an oxidizing agent to form acrolein;
(2) reacting acrolein with a molecular halogen to form 2,3-dihalopropanal;
(3) reducing 2,3-dihalopropanal to form 2,3-dihalopropanol as described in the first aspect of the invention; and
(4) cyclizing 2,3-dihalopropanol to make epihalohydrin.

The process in the second aspect of the invention produces epihalohydrin using only about one mole of molecular halogen per mole of epihalohydrin. This process reduces the amount of halogenated organics in the waste stream by more than 60 percent, relative to the commercial allyl chloride route. The process also uses substantially less water than existing processes. The reducing agent may be hydrogen, so that there is no need to recycle ketone, as in transfer hydrogenation.

DETAILED DESCRIPTION OF THE INVENTION

The present invention makes 2,3-dihalopropanol from a 2,3-dihalopropanal, which preferably is represented by:

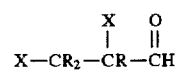

Formula II $$X-CR_2-CR(X)-CH(=O)$$

wherein:

each "X" is independently a halogen, is preferably chlorine or bromine and is most preferably chlorine; and
each "R" is independently hydrogen or a lower ($C_1$ to $C_6$) hydrocarbyl group, is preferably hydrogen or a lower alkyl group, is more preferably hydrogen or a methyl group and is most preferably hydrogen.

Examples of suitable 2,3-dihalopropanals include: 2,3-dichloropropanal; 2,3-dibromopropanal; 2,3-dichloro-2-methylpropanal and 2,3-dibromo-2-methylpropanal. The 2,3-dihalopropanal is most preferably 2,3-dichloropropanal.

The dihalopropanal is hydrogenated by reaction with a hydrogen source. The hydrogen source is highly preferably molecular hydrogen, but other suitable hydrogen sources include alcohols, which are preferably secondary alcohols.

The reaction consumes one mole of molecular hydrogen per mole of dihalopropanol which is made. (For convenience, the term "molecular hydrogen" encompasses equivalent hydrogen sources which yield two hydrogen atoms per molecule, such as secondary alcohols.)

Preferably at least about 0.75 moles of molecular hydrogen per mole of 2,3-dihalopropanal are available during the course of the reaction, more preferably at least about 0.9 moles and most preferably at least about 1 mole. When less than 1 mole of molecular hydrogen per mole of 2,3-dihalopropanal is available during the course of the reaction, the reaction is less efficient because complete conversion of the 2,3-dihalopropanal is not obtained. However, not all of the hydrogen need be available at the start of the reaction. Hydrogen may be added step-wise or continuously as the reaction progresses. In this case, the reaction mixture at any one time may contain a stoichiometric excess of dihalopropanal over hydrogen.

The maximum quantity of hydrogen source is not critical and is governed by practical considerations such as pressure, reactor efficiency and safety. When the hydrogen source is gaseous, then the quantity of hydrogen is preferably at least enough to provide the desired pressure. However, in most cases, the reactor preferably contains no more than about 1,000 moles of molecular hydrogen per mole of 2,3-dihalopropanal and more preferably contains no more than about 100 moles. Gaseous hydrogen sources, such as molecular hydrogen, are preferably used according to known methods for mixing a gaseous reagent with a liquid reaction mixture, such as bubbling the gas through the mixture with agitation or solubilizing the hydrogen under pressure.

The reaction takes place in the presence of a transition metal-containing catalyst. By transition metal, we mean a metal selected from any of Groups IB, IIB or IIIA-VIIIA on the periodic table of elements, as currently adopted by the International Union of Pure and Applied Chemistry (IUPAC), which is incorporated herein by reference. The catalyst metal is selected such that under reaction conditions it hydrogenates substantially all of the aldehyde moieties to primary alcohol moieties without substantially affecting the halogens which are bonded to the molecule. The catalyst metal is preferably selected from Group VIIIA of the periodic table: cobalt, nickel, copper, ruthenium, rhodium, palladium, osmium, iridium and platinum. It is more preferably ruthenium, nickel, palladium or platinum and is most preferably ruthenium.

The transition metal catalyst may be in homogeneous or heterogeneous form. The transition metal in the catalyst may be in an oxidized or unoxidized state. For example, a homogeneous catalyst may contain a transition metal salt or a soluble coordination compound of the transition metal with a solubilizing ligand. Also, for example, a heterogeneous catalyst may contain transition metal deposited or absorbed on an inorganic support such as carbon, or it may contain a resin having transition metal carboxylate or carbonate moieties. Examples of transition metal salts include the metal halides, acetates and hydroxides.

Homogeneous catalysts preferably further contain a coordinating ligand. Examples of suitable coordinating ligands include phosphines, arsines, stibines, carbon monoxide, ethers and aromatic amines. Examples of suitable phosphines include, in particular, triaryl phosphine and more particularly triphenyl phosphine. The optimum concentration of coordinating ligand varies, depending upon the catalyst metal, the ligand, and the desired activity of the catalyst in a manner which is familiar to persons of ordinary skill in the art. It can readily be determined without undue experimentation. When the transition metal is ruthenium and the ligand is a phosphine, the molar quantity of ligand per mole of metal is preferably at least about 0.01, more preferably at least about 1 and most preferably at least about 2. The molar ratio is preferably no more than about 1,000, more preferably no more than about 100 and most preferably no more than about 10.

The preferred concentration of homogeneous catalyst varies widely depending upon the catalyst selected and its activity. For most homogeneous catalysts, the reaction mixture preferably contains at least about 0.01 mmoles of catalyst metal per mole of dichloropropanal, more preferably at least about 1 mmole and most preferably at least about 4 mmoles. The maximum concentration of homogeneous catalyst is not critical and is limited primarily by practical limits, such as cost. Usually, the catalyst metal concentration is preferably no more than about 100 mmoles per mole of dichloropropanal, more preferably no more than about 25 mmoles and most preferably no more than about 10 mmoles.

For heterogeneous catalysts, the ideal ratio of catalyst to reagents varies depending upon flow rate, bed size, temperature, desired conversion, reagents and other factors. Usually, a heterogeneous catalyst bed contains about 0.01 to 1,000 mmoles of catalyst metal for each mole of dichloropropanal which passes through the bed per hour.

The reaction is preferably carried out in the presence of a protic solvent. Examples of protic solvents include water, carboxylic acids, phenolic compounds and aliphatic alcohols. The protic solvent is preferably water or an aliphatic alcohol and more preferably water or an alkanol. The alcohol preferably contains about 1 to 12 carbon atoms, more preferably contains about 1 to 6 carbon atoms and most highly preferably contains about 1 to 3 carbon atoms. Examples of suitable alcohols include methanol, ethanol, propanol and 2,3-dichloropropanol.

We theorize, without intending to be bound, that the protic solvent activates the reduction. However, alcohols also participate in certain competing side reactions in the presence of an acid. Therefore, it is preferable to either: (a) minimize the concentration of protic solvent to the lowest level at which the reaction will run with a desired rate, or (b) run the reaction in the presence of an acid scavenger. The molar ratio of alcohol to dichloropropanal is preferably at least about 0.9:1 and no more than about 200:1. The optimum ratio within this range varies depending upon the presence or absence of acid scavenger and the conditions of the reaction—particularly the temperature. Higher temperatures often work better with higher alcohol concentration.

The reaction is preferably carried out in the presence of an additional aprotic solvent. The aprotic solvent is preferably inert with respect to all of the reagents under the reaction conditions. It may be selected such that: (1) it does not boil under reaction conditions; and (2) 2,3-dichloropropanol can be recovered from it by distillation. Examples of suitable solvents include aromatic and aliphatic hydrocarbons, ethers, glymes and glycol ethers. The quantity of solvent is not critical and is governed primarily by practical considerations, such as the ability to dissolve the catalyst and the efficiency of the reactor. In most cases, the reaction mixture preferably contains at least about 5 weight percent 2,3-dihalopropanal, more preferably at least about 10 weight percent and most preferably at least about 20 weight percent. The reaction can be neat (about 100 weight percent 2,3-dihalopropanal), but as a solvent is used, the reaction mixture preferably contains no more than about 90 weight percent dihalopropanal and more preferably no more than about 80 weight percent.

When the reaction mixture contains an alcohol, the reaction is preferably carried out under conditions which are substantially free of strong mineral acids such as hydrogen chloride, which may cause a reduction in selectivity and yields. By substantial absence, we mean that the concentration of such acids is low enough that they do not catalyze the formation of acetals. For instance, the pH of the reaction mixture is preferably at least about 4, more preferably at least about 5 and most preferably at least about 6. It is preferably at most about 9 and more preferably at most about 8.

We theorize, without intending to be bound, that strong acid catalyzes the reaction of 2,3-dichloropropanal and methanol to form an undesirable acetal. The reaction mixture frequently contains minor quantities of hydrogen halide, and so the reaction is preferably carried out in the presence of an acid scavenger if alcohol is present. Examples of suitable acid scavengers include alkali metal carbonate, alkali metal bicarbonate and epoxides. Epichlorohydrin is the preferred epoxide to serve as an acid scavenger.

The temperature of the reaction is not critical, provided that all of the reagents, aside from the hydrogen, remain liquid and in contact with each other. However, low temperatures require longer reaction times and lead to increased levels of impurities. The reaction temperature is preferably at least about −10° C., more preferably at least about 20° C. and most preferably at least about 50° C. The reaction temperature is preferably less than about 250° C., more preferably no more than about 100° C. and most preferably no more than about 85° C.

The reaction pressure is not critical as long as there is sufficient hydrogen to run the reaction in the reaction mixture. The pressure is preferably at least about 14 psi (97 kPa, 1 atmosphere) and more preferably at least about 50 psi (340 kPa, 3.4 atmospheres). The pressure is preferably no more than about 3,000 psi (21 MPa, 220 atmospheres). Higher pressures lead to shorter reaction times.

The product of the reaction is a 2,3-dihalopropanol with a structure derived from the 2,3-dihalopropanal. It may be recovered by known methods, such as extraction or distillation. It is preferably recovered in at least about 80 percent yields (based upon the initial quantity of 2,3-dihalopropanal), more preferably in at least about 90 percent yields and most preferably in at least about 95 percent yields.

The reaction is particularly useful in a four-step process to make epichlorohydrin from propylene.

In Step (1), a 3-carbon hydrocarbon such as propylene is oxidized to form acrolein. Processes for this reaction are already well-known in the art and are described in the following references, which are incorporated herein by reference: Watanabe et al. (U.S. Pat. No. 4,008,281 (Feb. 15, 1977)); Childress et al. (U.S. Pat. No. 4,049,577 (Sep. 20, 1977)); Childress et al. (U.S. Pat. No. 4,129,600 (Dec. 12, 1978)); Daumas et al. (U.S. Pat. No. 4,166,808 (Sep. 4, 1979)); Caillod et al. (U.S. Pat. No. 5,225,389 (Jul. 6, 1993)) and Kobayashi et al. (U.S. Pat. No. 5,326,916 (Jul. 5, 1994)). In most cases, propylene is contacted in a gaseous phase with oxygen in the presence of a catalyst such as bismuth-phosphorous-molybdenum. Acrolein can also be made by oxidation of allyl alcohol or by heating glycerol with magnesium sulfate. Acrolein is also commercially available.

In Step (2), acrolein is halogenated to make 2,3-dihalopropanal. This step has been described in U.S. Pat. No. 2,860,146, which is incorporated herein by reference. Preferably, the acrolein is contacted with molecular halogen, which is preferably molecular chlorine or bromine and is more preferably molecular chlorine. The reaction temperature is preferably no more than about 125° C. and more preferably no more than about 50° C. It is preferably at least about −10° C. and more preferably at least about 0° C. The reaction can be run neat, but preferably takes place in the presence of an organic solvent which is inert with respect to all reagents under reaction conditions. Examples of suitable solvents include halogenated hydrocarbons, such as methylene chloride, 1,2-dichloroethane and 1,2-dichloropropane.

The concentration of water in the reaction mixture of Step (2) is preferably minimized because water reacts with the product to form impurities. This is particularly true when Step (3) is run in the presence of an alcohol, because water reacts with chlorine to form hydrogen chloride. When Step (3) uses alcohol, the concentration of water (as a percentage of acrolein) is preferably no more than about 2 weight percent, more preferably no more than about 1 weight percent and most preferably no more than about 0.5 weight percent. The minimum concentration is not critical. Although 0 percent is ideal, 0.1 weight percent maybe more practical. Water can be excluded by known processes, such as by freeze drying, by use of molecular sieves and/or by adding dehydrating agents. The reaction pressure is preferably about 20 to 30 psi. The yield of 2,3-dichloropropanal is preferably at least about 90 percent.

Step (3) is the reduction of 2,3-dihalopropanal to 2,3-dihalopropanol. The preferred embodiments of this step have been described previously in this application.

Step (4) is the conversion of 2,3-dihalopropanol to epihalohydrin. That step is well-known in the art of manufacturing epihalohydrin. It is usually carried out by contacting the dihalopropanol with a strong base, such as aqueous alkyl metal hydroxide. Examples of this reaction are described in U.S. Pat. No. 2,860,146 and Wernli et al. (Australian Patent 630,238 (Feb. 12, 1993)), which are incorporated herein by reference.

Processes which use our invention may contain any one or more of Steps (1), (2) and (4), in addition to Step (3). They preferably contain Steps (2) and (3), more preferably contain Steps (2), (3) and (4) and most preferably contain Steps (1)–(4).

EXAMPLES

The following examples are for illustrative purposes only and should not be taken as limiting the scope of either the Specification or the claims. Unless otherwise stated, all parts and percentages are by weight.

EXAMPLE 1

A solution containing 148 g of acrolein and 500 ml of methylene chloride is cooled to about 0° C. Chlorine is passed through the solution at atmospheric pressure with stirring and cooling to maintain the reaction mixture at below 18° C., until a slight yellow color of chlorine is observed to persist. The methylene chloride is distilled under reduced pressure to yield 253 g of 2,3-dichloropropanal, which is characterized by NMR.

A 300-ml Parr bomb reactor equipped with mechanical stirrer is loaded with: 5 g of 2,3-dichloropropanal, 100 ml of ethanol and 200 mg of tris(triphenylphosphine)ruthenium (II) chloride. The reactor is sealed and pressurized with about 250 psi hydrogen. The reactor is heated to 85° C. for three hours. The reactor is cooled and unreacted hydrogen is released. Ethanol is removed by distillation and the remaining oil is treated with 150 ml of 5 percent ethyl acetate in a mixture of hexanes. The solution is filtered through silica gel and hexane is distilled to yield 3.5 g (70 percent) of 2,3-dichloro-1-propanol.

EXAMPLES 2–5

A quantity of 2,3-dichloropropanal which is shown in Table I is added slowly to a mixture which contains a ruthenium catalyst as shown in Table I and any of: methanol, 1-cyclohexyl-2-pyrrolidinone, dioxane and water in the quantities shown in Table I. An exotherm is observed in Examples 2–4. The mixture is sparge degassed with nitrogen and placed in a 300 ml Parr reactor which has been evacuated and charged with nitrogen. The reactor is pressurized with hydrogen, relieved and then repressurized with hydrogen to about 1,000 psi (about 7 MPa) pressure. The reactor is heated to 85° C. for three hours. The reactor is cooled and unreacted hydrogen is released. In Example 2, methanol is rotary-evaporated off and the remaining liquids are distilled under reduced pressure to yield the quantity of 2,3-dichloropropanol in Table I. In Examples 3–5, the reaction mixture is analyzed by GC analysis using decane as an internal standard and contains the quantity of 2,3-dichloropropanol shown in Table I.

TABLE I

| Example | 2 | 3 | 4 | 5 |
|---|---|---|---|---|
| 2,3-dichloropropanol (g) | 50 | 5 | 5 | 1.3 |
| Catalyst | | | | |
| tris(triphenylphosphine) ruthenium (II) dichloride (g) | 2 | 0.2 | 0.2 | — |
| 5% ruthenium on carbon (g) | — | — | — | 5.44 |

TABLE I-continued

| Example | 2 | 3 | 4 | 5 |
|---|---|---|---|---|
| Solvents | | | | |
| 1-cyclohexyl-2-pyrrolidinone (g) | 10 | — | — | — |
| methanol (ml) | 50 | 100 | — | — |
| water (ml) | — | — | 2 | 0.8 |
| dioxane (ml) | — | — | 80 | 50.9 |
| Product 2,3-dichloropropanol | 46.1 g | 96% | 94% | 83% |

What is claimed is:

1. A process to make 2,3-dihalopropanol comprising the step of reacting 2,3-dihalopropanal with molecular hydrogen in the presence of a transition metal-containing catalyst, under conditions such that 2,3-dihalopropanol is formed.

2. The process as described in claim 1 wherein the catalyst contains a Group VIIIA metal.

3. The process as described in claim 2 wherein the catalyst contains ruthenium.

4. The process as described in claim 3 wherein the catalyst contains a ruthenium salt.

5. The process as described in claim 3 wherein the catalyst further contains a stabilizing ligand associated with the ruthenium compound.

6. The process of claim 5 wherein the ligand is a phosphine.

7. The process of claim 3 wherein the catalyst is a heterogeneous catalyst which contains ruthenium deposited upon a supporting material.

8. The process of claim 3 wherein the reaction mixture further contains water or a protic organic compound.

9. The process of claim 8 wherein the reaction mixture contains an alkanol which contains 1 to 12 carbon atoms.

10. The process of claim 8 wherein the reaction mixture contains water.

11. The process of claim 10 wherein the pH of the reaction mixture is at least about 5.

12. The process of claim 8 wherein the mixture further contains an additional aprotic solvent.

13. The process of claim 8 wherein the reaction mixture contains an acid scavenger.

14. The process of claim 13 wherein the acid scavenger is epichlorohydrin.

15. The process of claim 1 which is carried out at a temperature of about 0° C. to 200° C.

16. The process of claim 1 wherein the 2,3-dihalopropanal is unsubstituted 2,3-dichloropropanal.

17. A process of claim 1 comprising the step of contacting a 2,3-dihalopropanal with at least a stoichiometric quantity of molecular hydrogen in the presence of a ruthenium-containing catalyst and an alcohol, wherein the molar ratio of alcohol to dichloropropanal is no more than 5:1 or wherein the mixture further contains an acid scavenger.

18. A process of claim 1 comprising the step of contacting a 2,3-dihalopropanal with at least a stoichiometric quantity of hydrogen in the presence of a ruthenium-containing catalyst and water.

19. A process to make epihalohydrin comprising the steps of:

(a) halogenating acrolein to make 2,3-dihalopropanal;

(b) reducing-the 2,3-dihalopropanal as described in claim 18 to form 2,3-dihalopropanol; and (c) contacting the 2,3-dihalopropanol with a base, whereby an epihalohydrin is formed.

* * * * *